US010967092B2

(12) United States Patent
Chang

(10) Patent No.: US 10,967,092 B2
(45) Date of Patent: Apr. 6, 2021

(54) DIFFUSER FOR ESSENTIAL OILS

(71) Applicant: GREENAIR INC., Westlake, OH (US)

(72) Inventor: David T. Chang, University Heights, OH (US)

(73) Assignee: Greenair Inc., Westlake, OH (US)

( * ) Notice: Subject to any disclaimer, the term of this patent is extended or adjusted under 35 U.S.C. 154(b) by 232 days.

(21) Appl. No.: 16/386,334

(22) Filed: Apr. 17, 2019

(65) Prior Publication Data

US 2020/0330637 A1 Oct. 22, 2020

(51) Int. Cl.
| *A61L 9/14* | (2006.01) |
| *A61L 9/12* | (2006.01) |
| *B01F 3/04* | (2006.01) |
| *A61L 9/013* | (2006.01) |

(52) U.S. Cl.
CPC ............... *A61L 9/122* (2013.01); *A61L 9/013* (2013.01); *A61L 9/14* (2013.01); *B01F 3/04021* (2013.01); *A61L 2209/12* (2013.01); *A61L 2209/132* (2013.01)

(58) Field of Classification Search
CPC .... A61L 9/14; A61L 9/122; B01F 3/04; B01F 3/04099; B01F 3/04021
See application file for complete search history.

(56) References Cited

U.S. PATENT DOCUMENTS

| 9,078,938 B2* | 7/2015 | Hsiao ................ B05B 17/0615 |
| 9,211,357 B1* | 12/2015 | Li ............................. A61L 9/14 |
| 10,034,987 B2 | 7/2018 | Pitcher ............................... 11/2 |
| 2018/0099068 A1* | 4/2018 | Pitcher ................... F04B 13/02 |

OTHER PUBLICATIONS www.audiowell.com ; Aromatherapy has this way!; release time: Aug. 4, 2018.

* cited by examiner

*Primary Examiner* — Robert A Hopkins
(74) *Attorney, Agent, or Firm* — Renner Kenner Greive Bobak Taylor and Weber

(57) ABSTRACT

A diffuser includes a housing with at least one inlet and at least one vent outlet, and a microblower carried by the housing. The microblower has an inlet side to receive air from the at least one inlet, and an outlet port. A bottle adapted to carry essential oil is included and has a neck opening. A tube directs air from the microblower outlet port into the neck opening to generate oil-laden air. A fan draws ambient air in from the at least one inlet and exhausts ambient air and oil-laden air through the at least one vent outlet.

15 Claims, 3 Drawing Sheets

DIFFUSER FOR ESSENTIAL OILS

TECHNICAL FIELD

Generally, the present invention is directed toward diffusers. Specifically, the present invention is directed to essential oil diffusers, wherein a microblower assists with airflow of the essential oil within the diffuser and a fan generates added airflow to complete the diffusion process.

BACKGROUND ART

It is well known that aromatherapy utilizes plant materials and aromatic plant oils which are dispersed by a diffuser. In particular, essential oils are used for the purpose of calming and relaxing those in the vicinity of the diffuser. It is also believed that aromatherapy utilizing essential oils may assist in healing.

One common method of dispersing an essential oil is to utilize aerial diffusion wherein the essential oil is dispersed by passing an airflow over the oil or by gently warming the oil. It is also known to mix the essential oil with water in a diffuser reservoir, generate a vapor of the oil-water mixture by means of an ultrasonic transducer, and then distribute the vapor with a fan. However, the mixture dilutes the effectiveness of the oil and also requires repeated refilling of the diffuser reservoir. In other words, the reservoirs eventually run out of water which automatically triggers the diffuser to stop operating and thus no oil is dispersed, thereby limiting its effectiveness. The water and oil vapor mixture also potentially introduces unwanted humidity in the air.

Therefore, there is a need in the art for means to effectively diffuse the essential oil for longer periods of time without the need for a water-based diffusion system. Moreover, there is a need to effectively disperse the essential oil in a preliminary airflow and then utilize a second airflow to further amplify the preliminary airflow for a powerful aroma diffusion, using filtered air. There is also a need for combining an essential oil diffuser with an ion generator for air purification, which may be used anytime the essential oil diffuser is not operating or is selectively turned off by the user.

SUMMARY OF THE INVENTION

In light of the foregoing, it is a first aspect of the present invention to provide a diffuser for essential oils.

It is another aspect of the present invention to provide a diffuser, comprising a housing having at least one inlet, and at least one vent outlet, a microblower carried by the housing, the microblower having an inlet side to receive air from the at least one inlet and an outlet port, a bottle adapted to carry essential oil, the bottle having a neck opening, a tube directing air from the microblower outlet port into the neck opening to generate oil-laden air, and a fan drawing ambient air in from the at least one inlet and exhausting ambient air and oil-laden air through the at least one vent outlet.

Yet another aspect of the present invention is to provide a diffuser, comprising a housing having an inlet and an outlet, a bottle adapted to carry essential oil, the bottle carried by the housing, a microblower associated with the bottle to direct an airflow on to a surface of the essential oil to generate oil-laden air, and a fan drawing ambient air in through the inlet and exhausting ambient air and oil-laden air through the outlet.

BRIEF DESCRIPTION OF THE DRAWINGS

These and other features and advantages of the present invention will become better understood with regard to the following description, appended claims, and accompanying drawings wherein:

BEST MODE FOR CARRYING OUT THE INVENTION

Figure 1:
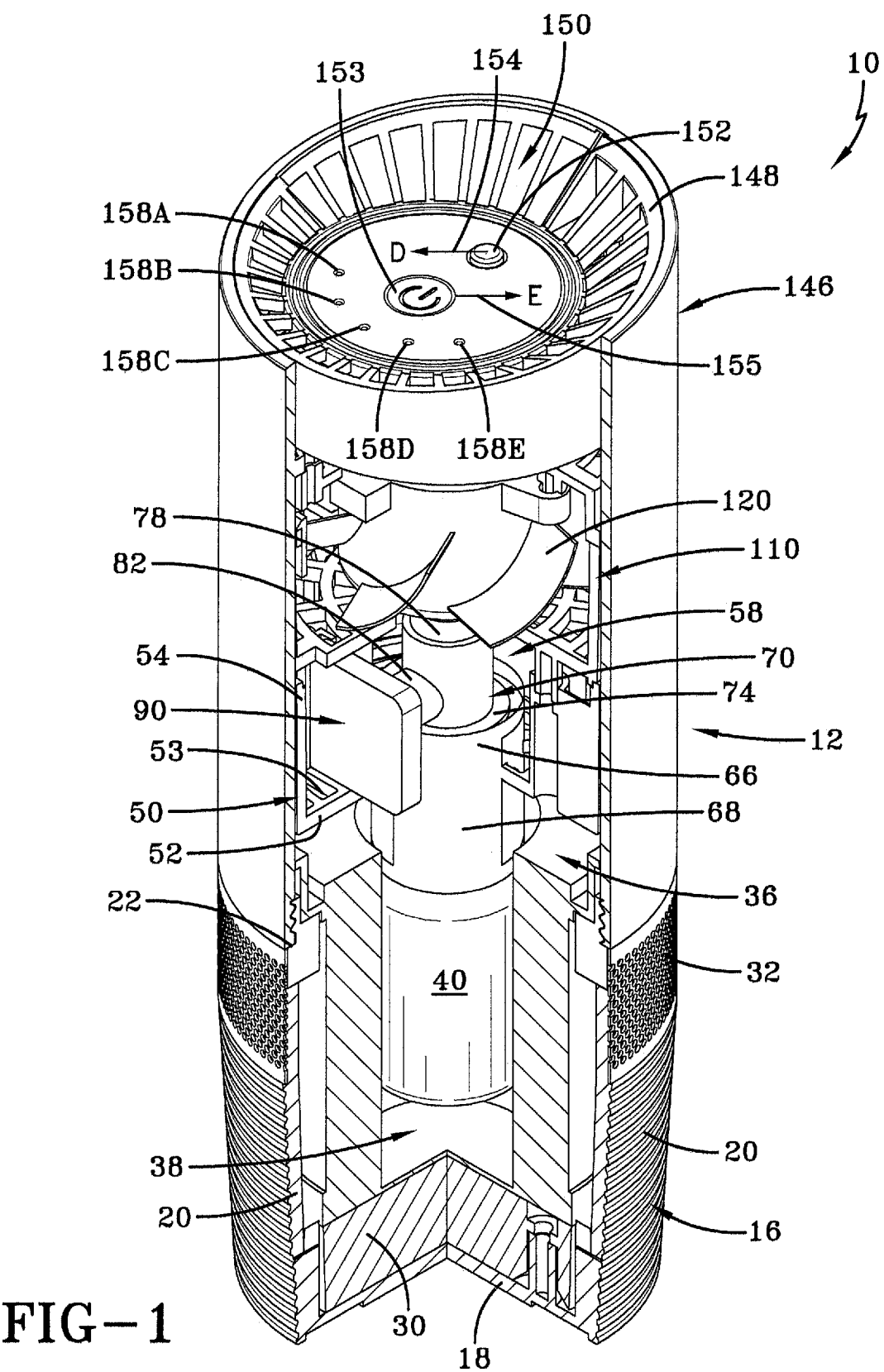
FIG. 1 is perspective view, in partial cross-section, of a diffuser according to the concepts of the present invention.
Figure 2:
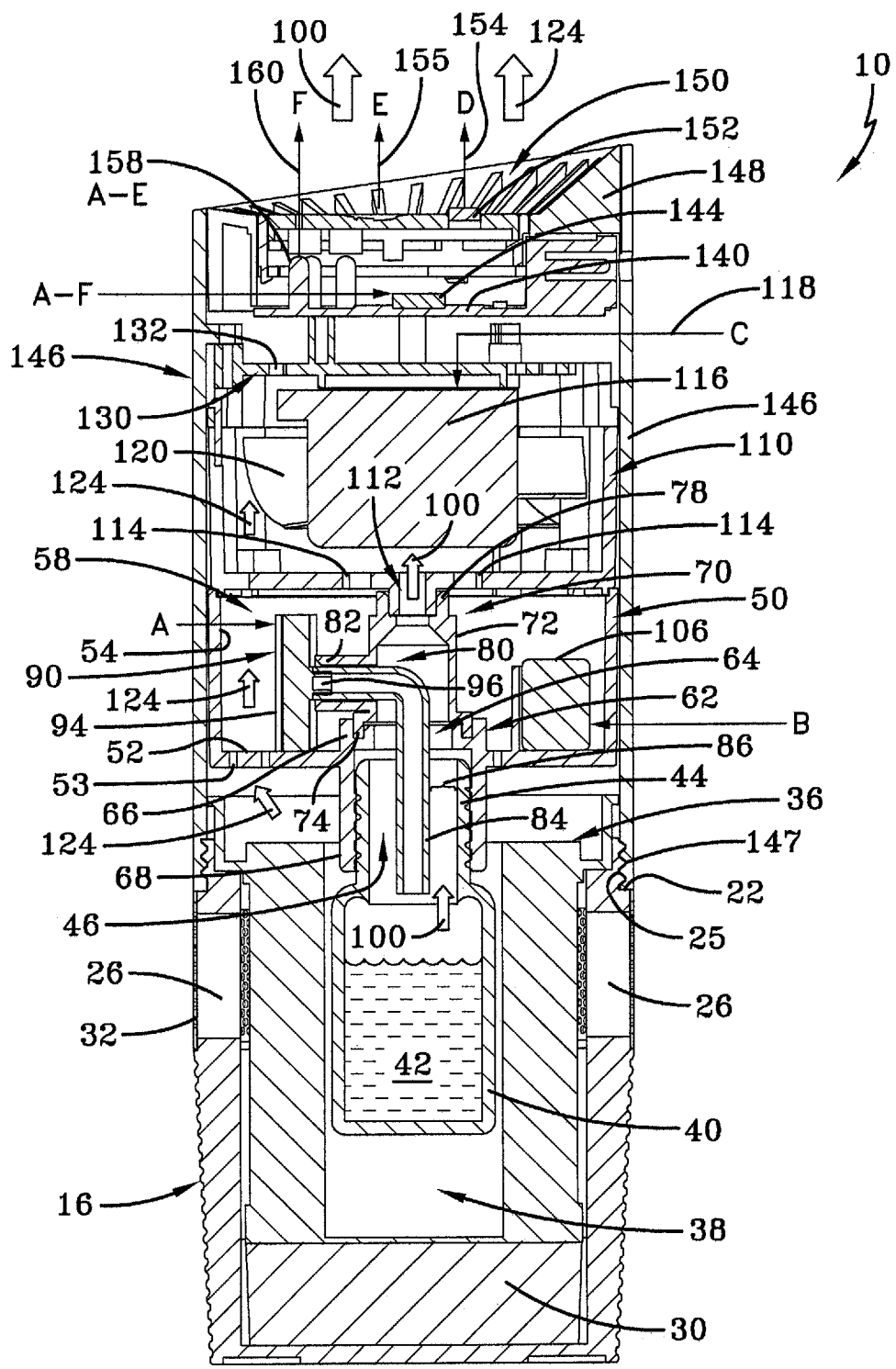
FIG. 2 is a cross-sectional view of the diffuser according to the concepts of the present invention.
Figure 3:
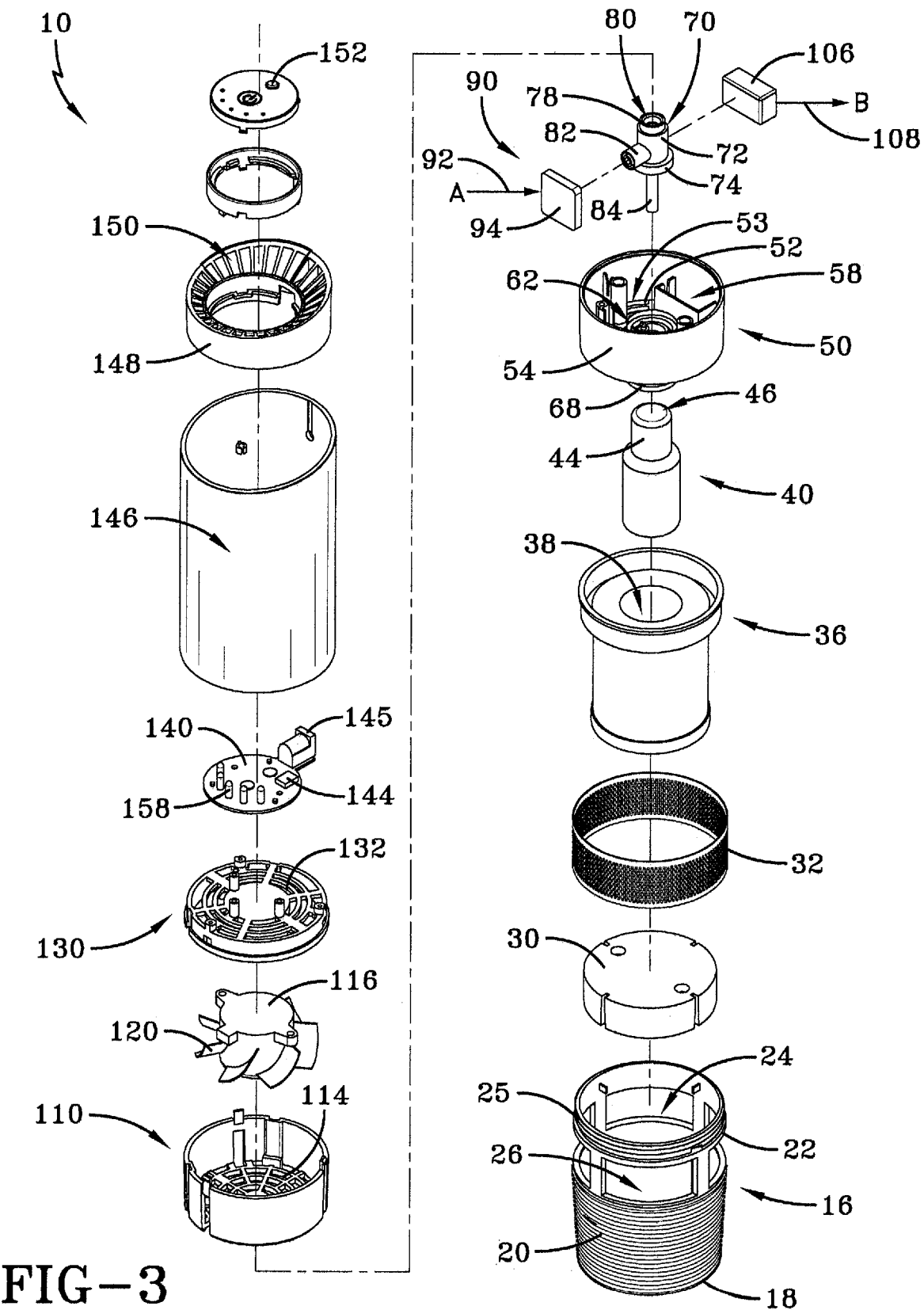
FIG. 3 is an exploded perspective view of the diffuser according to the concepts of the present invention.

Referring now to the drawings, it can be seen that a diffuser is designated generally by the numeral 10. Generally, the diffuser 10 employs a two-stage diffusion process. First, a microblower is utilized to generate an essential oil and air mixture, also referred to as oil-laden air, and then a diffuser fan is used to disperse the oil-laden air in combination with filtered air to ambient. It is believed that this configuration adequately diffuses the essential oils in an airborne mixture instead of a vapor so as to enhance the benefits of the essential oils. Additionally, the diffuser 10 may be configured to operate as an ionic filtration system.

The diffuser 10 provides for a housing 12 which includes multiple structural components for configuration of the housing. The housing 12 may include a base 16 which forms a lower portion of the housing wherein the base includes a bottom 18 with an upwardly extending sidewall 20. The sidewall 20 may provide for an internal lip 22 opposite the bottom, wherein the sidewall 20 forms an internal chamber 24. The sidewall 20, in the area of the lip 22, may provide external threads 25, which allow the base to be secured to other components of the housing 12. The sidewall 20 may be provided with a plurality of wall inlets 26 which allow for entry of ambient air into the housing for filtration as will be described. In some embodiments a weight 30 may be received in the chamber 24 so as to maintain the diffuser in an upright and working condition.

A mesh filter 32 may be positioned within or around the chamber 24 or around the base 16 and aligned with the wall inlets 26. The mesh filter 32 with filter openings may be of a cylindrical configuration with an opening therethrough such than an outer surface of the filter is substantially flush with an outer surface of the base 16 and an inner surface of the filter is positioned adjacent to or in close proximity with the inlets 26. The mesh filter 32 prevents coarse air particles or other pollutants carried in the ambient air from entering the housing 12. Also positioned within the chamber 24 on a side of the mesh filter 32 opposite the sidewall 20 may be a high-efficiency particulate air (HEPA) filter 36 which removes fine particulates or pollutants from the ambient air entering the housing 12. Other configurations of filters may be used in place of the HEPA filter. The filter 36 provides for an internal filter cavity 38.

An appropriately sized bottle 40, which contains essential oil 42, is received within the filter cavity 38. In the present embodiment the bottle 40 carries approximately one ounce of essential oil 42, although the diffuser and in particular the housing 12 may be sized as needed for different sizes of bottles. For example, some bottles may be sized to carry 5 ml, 10 ml, 15 ml, or any appropriate amount of oil. In any event, the bottle 40 provides for a neck 44 which provides for a neck opening 46. In the present embodiment an inner diameter of the neck opening is approximately 0.500 inches, but other inner diameter sizes may be employed.

A carrier 50 may be positioned on and at least partially supported by the bottle 40. In the present embodiment, the carrier 50 is of a generally cylindrical configuration although other appropriately shaped configurations may be used so as to allow nesting receipt of the carrier in the housing 12. The carrier 50 includes a plate 52 which may have an upwardly extending outer wall 54 at an outer periphery of the plate 52. The plate 52 may provide for a plurality of flow openings 53 so as to provide an entry point for airflow, wherein the airflow may be filtered or not, from the wall inlets 26 through the housing 12. The outer wall 54 forms a cavity 58. Extending through the plate 52, within the cavity 58, may be a collar 62 which forms a collar opening 64 therethrough. The collar 62 provides for an upper collar wall 66 which extends upwardly from the plate 52 and a lower collar wall 68 which extends downwardly from the plate 52. In the embodiment shown, an inner surface of the lower collar wall 68 may frictionally engage the exterior or outer diameter of the neck 44. Skilled artisans will appreciate that the housing 12 and the carrier 50 may be disassembled from each other and other components so as to allow for insertion of different essential oil bottles into the lower collar wall 68.

A manifold 70 may be received within the cavity 58 and in particular the manifold may be coupled to the upper collar wall 66. The manifold 70 provides for a wall 72 wherein the wall has a collar fitting 74 at one end which is coupled to or positioned in close proximity to the upper collar wall 66. The fit between the collar fitting 74 and the upper collar wall 66 is sufficient to result in an increased pressure within the bottle as will be described. The wall 72 also provides for a manifold outlet 78 at an end opposite the collar fitting 74. Extending through the manifold, from the collar fitting 74 to the manifold outlet 78, and substantially formed by the wall 72 is an aperture 80. The manifold also may provide for a manifold inlet 82 which extends through one side of the wall 72 and into the aperture 80. In the present embodiment, an inlet tube 84 is received in the manifold inlet 82 and extends downwardly through the aperture 80 and through the collar fitting 74. And in the present embodiment, the inlet tube 84 is made from a flexible polymeric material, but other embodiments may employ a rigid tube made of any material. The inlet tube 84 may be receivable into the neck opening 46. The inlet tube 84 may be sized to have an outer diameter which is smaller than an inner diameter of the neck opening. In the present embodiment there is a clearance of at least 0.010 inches between the outer diameter of the inlet tube 84 and the inner diameter of the neck 44. In other words, the outer diameter of the inlet tube 84 and the inner diameter of the neck 44 define a clearance 86 therebetween. The inlet tube 84 may be concentrically aligned with the neck 44, but in some embodiments the outer surface of the inlet tube may touch the inner surface of the neck 44 as long as a sufficient clearance to permit airflow is provided between the surfaces. Skilled artisans will appreciate that the manifold 70 may have an internal structure which eliminates the need for an inlet tube.

A microblower 90 may be carried on the plate 52 and positioned away from an inner surface of the outer wall 54. The microblower 90 utilizes a transducer sheet such that an applied voltage bends the sheet to change the volume within a pump chamber maintained by the blower. Accordingly, as the pump chamber volume increases, the pressure in the chamber decreases, and ambient air or the other input gas flows into the pump chamber. As the pump chamber volume decreases, by energizing or de-energizing the transducer sheet, the chamber pressure increases and forces the ambient air or other gas out of the pump chamber. The microblower is electrically operated and receives a blower signal 92 which is also designated in the drawing as capital letter A. The amount or flow of ambient air or other gas generated by the microblower may be controlled by the amount of voltage applied to the transducer sheet or by other voltage signal adjustments. The microblower 90 may have an inlet side 94 which faces the inner surface of the outer wall 54 and is positioned so as to receive ambient or filtered air that has passed through the mesh filter 32 and/or the HEPA filter 36. In most embodiments, filtered air from the filter 36 is delivered to the microblower's inlet side 94. The microblower 90 may also provide for an outlet port 96 which may be directly connected to the inlet tube 84. In other embodiments, an entry end of the tube may be placed close enough to collect air flow generated by the blower to allow transfer of the airflow through the length of the tube.

When energized, the microblower 90 draws air in through the inlet side 94 and directs that air through the outlet port 96 into the tube which has its opposite end placed in the bottle 40. Accordingly, as will be described in further detail below, the microblower generates an airflow that is directed through the inlet tube which is then directed into the bottle 40. In some embodiments, the end of the inlet tube does not contact the oil or a surface of the oil, but instead directs the airflow into the bottle so as to cause the air within the bottle to become pressurized and thus expel the pressurized air containing microscopic or other appropriately sized essential oil droplets through the clearance 86 and into aperture 80 of the manifold 70. In other embodiments, the manifold 70 may have an internal structure that directs the airflow from the outlet port 96 in such a way to pressurize the air within the bottle 40 to allow the pressurized air containing appropriately sized essential oil droplets into the aperture of the manifold. In either embodiment, the manifold serves as a conduit to generate oil-laden airflow 100 for further diffusion which is then expelled out the manifold outlet 78.

The carrier, and in particular the plate 52, may also support a negative ion generator 106. In the present embodiment, the generator 106 may be positioned diametrically opposite the microblower 90, but it may also be positioned substantially anywhere on the plate 52, or anywhere where airflow may pass in or around the generator's surface area. The negative ion generator is operated by a signal 108 which is also designated in the drawing as capital letter B. The generator 102, which may also be referred to as an ionizer, generates negative ions which are attracted to airborne particles which in turn are attracted to nearby grounded surfaces once expelled from the housing 12. As a result, the airborne particles, which may contain airborne bacteria, are removed from ambient air.

Positioned above the carrier 50 within the housing 12 is a fan/motor compartment 110. The compartment 110 provides for a motor inlet port 112 which is connected, or in close proximity, to the manifold outlet 78 so as to receive oil-laden airflow 100 therefrom. The fan/motor compartment 112 may be provided with air input ports 114 therethrough which receive filtered airflow 124 that passes from the mesh filter 32 and the HEPA filter 36 via the flow openings 53. A motor 116 may be carried by the fan/motor compartment and is energized by a signal 118 also designated in the drawing as capital letter C. The motor 116 drives and rotates a fan 120 with appropriately sized and shaped vanes so as to generate airflow through the housing 12. In particular, rotation of the fan draws ambient air in through the mesh filter 32, the inlets 26, and through the HEPA filter 36, which may be referred to as filtered airflow 124. Some of the filtered airflow 124 may be directed into the carrier 50 so as to pass in proximity to the microblower 90 and/or the negative ion generator 106. Airflow which is not directly exposed to either the microblower 90 or the generator 106 passes into the input ports 114 whereupon rotation of the fan directs that air through the remainder of the housing. Additionally, the fan 120 may receive airflow from the motor inlet port 112 which contains the oil-laden airflow 100 from the manifold 70. As a result, rotation of the fan 120 moves a combination of oil-laden airflow 100 and filtered airflow 124. Skilled artisans will appreciate that the oil-laden airflow intermixes with the filtered airflow 124 and is then expelled out the housing as will be discussed.

A fixture 130 may hold the fan/motor compartment 110 within the motor compartment in place. The fixture may provide for fixture openings 132 so as to allow the combination airflows to pass therethrough. Carried by the fixture 130 may be a circuit board 140 which carries a controller 144 and an appropriate battery or power supply connection. The controller 144 provides the necessary hardware, software, and memory so as to control operation of the diffuser 10. At a minimum, the controller energizes the microblower via signal A, the motor 116 via signal C, and the negative ion generator 106 via signal B as appropriate. The controller 144 may also receive various types of user inputs so as to control operation of the selected components. The circuit board may also provide a power supply input 145 to provide electrical power to the various components of the diffuser. Power may also be supplied by batteries.

An outer cover 146 may fit over the fixture 130, the fan/motor compartment 110, the carrier 50, and attach to the base 16, and in particular the sidewall 20 so as to fully enclose the aforementioned components. A lower edge of the cover 146 may provide internal threads 147 which mate with the external threads 25 to allow for assembly of the cover 146 to the base 16. The outer cover 146 may provide for a vent plate 148 which provides for a plurality of vent outlets 150 therethrough to allow for the filtered air 124 and oil-laden air 100 combination to be expelled out the housing.

The vent plate 148 may also carry a negative ion switch 152 and a power switch 153. The negative ion switch 152 generates a signal 154 also designated in the drawing as capital letter D, and the power switch 153 generates a signal 155 also designated in the drawing as capital letter E. Also associated with the fixture 130 and/or the vent plate 148 may be a plurality of lights, which in the present embodiment are LED lights 158 A-E and which are controlled by corresponding signals 160 which are designated in the drawing as capital letter F. A user may control operation of the diffuser by manually activating any one or combination of the switches 152 and 153, wherein the lights provide a visual feedback to designate the various operational states or conditions of the diffuser.

For example, in the configuration shown in FIG. 1, the negative ion switch 152, also referred to as an ion cycle button, controls a negative ion cycle, and the power switch 153, also referred to as a power cycle button, controls a power cycle. The lights and the switches may be provided with indicia to indicate the operating condition of the diffuser 10. In the present embodiment, light 158A may be associated with the word "AROMA;" light 158B may be associated with the abbreviation "MED," which indicates a medium fan speed; light 158C may be associated with the word "HI," which indicates a high fan speed; light 158D may be associated with the word "PURIFY," which indicates operation of the microblower or the negative ion generator; and light 158E may be associated with the word "IONIC," which indicates operation of the ion generator. Accordingly, actuation of the power button 153 will turn on the microblower 90 and the fan 120 at a low speed. This actuation will also automatically turn off the ion generator 106. In this arrangement, the light 158A designating aroma and the light 158D designating purify are illuminated. A second activation of the power button 153 will maintain the microblower 90 in an on condition, increase the speed of the fan 120 to medium, and maintain the ion generator 106 in an off condition. In this configuration the lights 158A, 158B, and 158D are illuminated. A third touch of the power button 153 will maintain the microblower 90 in an on condition; increase the speed of the fan 120 to high; and maintain the ion generator 106 in an off condition. In this configuration, the lights 158A, 158C, and 158D are illuminated. A fourth touch of the power button 153 will turn off the microblower 90, the fan 120, and the ion generator 106 will remain in an off condition. In this configuration none of the lights are illuminated.

Actuation of the negative ion cycle button 152 will place the microblower 90 in an off condition, place the fan 120 in a low speed condition, and the ion generator 106 is placed in an on condition. In this configuration, the lights 158D and 158E are illuminated. A second press of the ion cycle button 152 maintains the microblower 90 in an off condition and the fan 120 is elevated to a medium speed. The negative ion generator 106 is maintained in the on condition. The lights 158B, 158D, and 158E are illuminated. A third press of the ion cycle button 152 keeps the microblower 90 in an off condition, elevates the speed of the fan 120 to a high condition, and maintains the negative ion generator 106 in an on condition. In this configuration, the lights 158C, 158D, and 158E are illuminated. A fourth press of the ion cycle button 152 turns off all of the components, the fan 120 and the ion generator 106, and the microblower 90 remains in the off condition.

In any of the configurations above and at any given time, if the ion cycle button 152 is pressed, the diffuser will cut over to the negative ion cycle. In a similar manner, if the power switch 153 is pressed, the diffuser will switch over to the power cycle. Skilled artisans will appreciate that other user interface configurations may be implemented so as to control operation of the microblower 90, the fan 120, and the ion generator 106. However, despite the foregoing, skilled artisans will appreciate that the microblower 90 and ion generator 106 will likely never operate simultaneously as the ion generator will likely interfere with operation of the microblower 90 and its dispersal of oil-laden air.

In operation, the user will first insert a selected essential oil bottle 40 into the chamber 24. The carrier 50, which may be preassembled with other components such as the generator 106, is associated with the bottle 40 by a frictional or close fit between the lower collar wall 68 and the bottle neck 44. The preassembled carrier may include the microblower 90 wherein the outlet port 96 is connected or associated with the manifold and the inlet tube 84. The opposite end of the tube is directed through the aperture 80 in such a way that it is inserted into the neck 44 where the inlet tube may or may not contact the oil. The carrier 50 may also provide a frictional or close fit between the collar fitting 74 of the manifold 70 and the upper collar wall 66. In any event, skilled artisans will appreciate that the inlet tube is positioned within the neck so as to assist the microblower in pressurizing the air within the bottle an appropriate amount. The remaining components of the housing are then assembled onto the carrier 50 including the motor/fan compartment and the outer cover 146 and vent plate 148. At this time, the user will select the various settings provided by actuating the switch 152 and/or switch 152, which may be used to control the motor speed associated with the microblower and/or fan as described above. Accordingly, the fan and/or the microblower may be operated at various speeds such as low, medium, high, or any other speed deemed appropriate. The user may also select to operate the microblower or may select to operate the negative ion generator. The controller will be configured such that the microblower and negative ion generator do not operate at the same time. In other words, the microblower will operate exclusively of the negative ion generator, and likewise the negative ion generator will operate exclusively of the microblower. As a result, only one of these two devices may be allowed operate at one time. Accordingly, the user is allowed to either implement the negative ion generator or diffuse essential oils, depending on their particular preference. The LED lights associated with the controller may be utilized to indicate the various operating modes and also indicate whether the device is on or off.

When the microblower 90 is operating, the pressurized air is directed through the inlet into the bottle, whereupon oil droplets are carried by the air through the manifold and drawn into the fan/motor compartment by the fan and then expelled out through the vent outlets 150. When the negative ion generator is operating, the airflow generated by the fan 120 is ionized and routed through the compartment 110 and out the vent outlets 150.

Based on the foregoing the advantages of the present invention are readily apparent. The diffuser is configured so as to generate a controlled and specific airflow into the diffuser bottle so as to diffuse the essential oils at their source without any further carrier, such as water, being added. This oil-laden air is then mixed in with filtered ambient air for exhaustion out of the housing. This eliminates the use of water which requires refilling every several hours, and consumers are to enjoy the benefits of undiluted essential oil diffusion using purified air. The diffuser is also advantageous in that it can be implemented as a negative ion generator at the discretion of the user.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A diffuser, comprising:
a housing having at least one inlet, and at least one vent outlet;
a microblower carried by said housing, said microblower having an inlet side to receive air from said at least one inlet and an outlet port;
a bottle adapted to carry essential oil, said bottle having a neck opening;
a tube directing air from said microblower outlet port into said neck opening to generate oil-laden air; and
a fan drawing ambient air in from said at least one inlet and exhausting ambient air and oil-laden air through said at least one vent outlet.

2. The diffuser according to claim 1, further comprising:
a negative ion generator carried by said housing, wherein said microblower and said negative ion generator are configured so that each operates exclusively of the other.

3. The diffuser according to claim 2, wherein said fan operates when either said negative ion generator or said microblower operates.

4. The diffuser according to claim 1, further comprising:
a carrier maintained in said housing, said carrier having a plate with a collar which has a collar opening therethrough, said collar sized to fit around said neck opening.

5. The diffuser according to claim 4, further comprising:
a manifold having a wall with an aperture therethrough with a collar fitting at one end which fits onto said collar opening, and a side inlet extending through said wall, wherein said tube extends through said inlet and said collar opening into said neck opening.

6. The diffuser according to claim 5, further comprising:
a fan/motor compartment to carry said fan and having a motor inlet port coupled to said aperture to receive oil-laden air and at least one filtered air input to receive ambient air.

7. The diffuser according to claim 6, wherein the ambient air passes over said negative ion generator.

8. A diffuser, comprising:
a housing having an inlet and an outlet;
a bottle adapted to carry essential oil, said bottle carried by said housing;
a microblower associated with said bottle to direct an airflow on to a surface of the essential oil to generate oil-laden air; and
a fan drawing ambient air in through said inlet and exhausting ambient air and oil-laden air through said outlet.

9. The diffuser according to claim 8, further comprising:
a conduit interposed between said microblower and said bottle to deliver air to the bottle and oil-laden air for diffusion by the fan.

10. The diffuser according to claim 8, further comprising:
a negative ion generator carried by said housing, said negative ion generator disabled from operating whenever said microblower is operating.

11. The diffuser according to claim 10, further comprising:
a manifold interposed between said microblower and said bottle, said manifold having a manifold inlet to receive ambient air from said microblower for entry into said bottle, and a manifold outlet to direct oil-laden air into said exhausted ambient air.

12. The diffuser according to claim 11, further comprising:
an inlet tube extending from an outlet port provided by said microblower into said bottle.

13. The diffuser according to claim 12, wherein said bottle has a neck to receive said inlet tube, and wherein an outer diameter of said inlet tube is less than said neck's inner diameter.

14. The diffuser according to claim 13, wherein said inlet tube's outer tube has a clearance of at least 0.010" from said necks' inner diameter.

15. The diffuser according to claim 12, further comprising:
a filter interposed between said housing inlet and an inlet side of said microblower.

* * * * *